United States Patent [19]

Graf et al.

[11] 4,058,529

[45] Nov. 15, 1977

[54] POLYCYCLIC AMINO DERIVATIVES OF PYRROLIDONE AND PIPERIDONE

[75] Inventors: Wilfried Graf, Binningen; Erich Schmid, Basel, both of Switzerland

[73] Assignee: Ciba-Geigy Corporation, Ardsley, N.Y.

[21] Appl. No.: 429,911

[22] Filed: Feb. 2, 1965

[30] Foreign Application Priority Data

Feb. 11, 1964  Switzerland .......................... 1632/64

[51] Int. Cl.$^2$ ................. C07D 239/10; C07D 487/04; C07D 487/12; C07D 487/22
[52] U.S. Cl. .......................... 260/251 A; 260/239 BC; 260/239.3 B; 260/251 Q; 260/256.4 F; 260/256.5 R; 548/324; 260/268 PC; 260/268 TR; 260/268 BC; 260/326.5 B; 260/293.54; 260/293.6; 424/246; 424/248.54; 424/251; 424/256; 424/273 R; 424/274; 544/58; 544/116; 544/119; 544/131; 544/139; 260/243.3; 424/248.55; 424/248.52; 424/248.5

[58] Field of Search .................. 260/251, 256.4, 256.5, 260/239 B, 239 BP, 251 A, 256.4 F, 256.5 R

[56] References Cited

U.S. PATENT DOCUMENTS

| 3,334,099 | 8/1967 | Houlihan | 260/251 |
| 3,334,113 | 8/1967 | Houlihan | 260/309.7 |

*Primary Examiner*—Raymond V. Rush
*Attorney, Agent, or Firm*—John J. Maitner

[57] ABSTRACT

A series of compounds of the formula

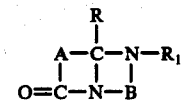

have been found to exhibit useful pharmacological properties, e.g. antiinflammatory and analgetic activity.

5 Claims, No Drawings

POLYCYCLIC AMINO DERIVATIVES OF PYRROLIDONE AND PIPERIDONE

The present invention concerns a process for the production of new, condensed heterocyclic compounds as well as the new compounds obtained by this process. It has surprisingly been found that heterocyclic compounds are obtained of the general formula I

wherein
- R₁ represents a low alkyl radical or an aryl or aralkyl radical which may be substituted, if desired, by low alkyl, alkoxy, alkylthio, alkylsulphonyl, alkylamino, dialkylamino, alkanoylamino, alkylsulphamyl or dialkylsulphamyl groups, hydroxyl, nitro, amino, sulpho, sufamyl or trifluoromethyl groups and/or by halogen atoms, or it represents a heteroaryl radical and
- R₂ represents hydrogen, a low alkyl radical substituted, if desired, by hydroxyl or amino groups, low alkoxy, alkylthio, alkylamino or dialkylamino groups, by polymethylenimino and alkyl-substituted polymethylenimino groups having 5–7 ring members, by a low 4-alkyl-1-piperazinyl group, the morpholino group or by the thiomorpholino group, or it represents an aralkyl radical, substituted, if desired, corresponding to the definition of R₁, and
- A and B represent divalent, optionally substituted aliphatic, cycloaliphatic, aromatic, araliphatic or heterocyclic radicals having 2 – 4 carbon atoms between the two valences but not more than 2 belonging to the same ring, and at least one of the radicals A and R₁ is aromatically or heteroaromatically bound to the central carbon atom, if a γ- δ- or ε-ketocarboxylic acid or a derivative thereof corresponding the general formula II

wherein
X represents the hydroxyl group, chlorine or bromine or a low alkoxy group or alkanoyloxy group, in particular the acetoxy group, and
R₁ and A have the meanings given in general formula I,
which compound can also be wholly or partially in the tautomeric form corresponding to general formula III

is reacted with a compound of general formula IV $$H_2N - B - NH - R_2 \quad (IV)$$

wherein B and R₂ have the meanings given in general formula I.

The new compounds produced in a simply way by this process, generally in good yields, are surprisingly distinguished by valuable pharmacological properties. In particular such compounds have anti-inflammatory, anaesthesia-potentiating, anti-convulsive and analgetic activity with, at the same time, relatively slight toxicity.

The anti-inflammatory activity of the compounds of general formula I can be seen, for example, from tests made on animals suffering from peritonitis induced by formalin. On administration of 200 mg per kg body-weight per os to rats, the following compounds, for example, caused a reduction of exudation of more than 45% compared with control animals: 7a-phenylhexahydro-5H-pyrrolo[1,2-a]imidazol -5-one, 8a-(p-chlorophenyl)-hexahydro-5H-pyrrolo[1,2-a]pyrimidin-6(2H)-one, 9b-(p-chlorophenyl)-1,2,3,9b-tetrahydro-5H-imidazo[2,1-a]isoindole-5-one, 1-methyl-9b-phenyl-1,2,3,9b-tetrahydro-5H-imidazo[2,1-a]isoindole 5-one and 1-ethyl-9b-phenyl-1,2,3,9b-tetrahydro-5H-imidazo[2,1-a]isoindole-5-one. Similar favourable results are also obtained, e.g. in tests regarding the influence of oedema of the rat's paw induced by formalin and by albumin as well as in tests regarding reduction of pyrexia in the rat.

The compounds of general formula I form salts having, in general, moderately to good water solubility, with inorganic and organic acids such as, e.g. hydrochloric acid, hydrobromic acid, sulfuric acid, tartaric acid, citric acid, maleic acid, fumaric acid, ascorbic acid, salicyclic acid, and acetylsalicylic acid.

The ions of these acids do not impart pharmaceutically unacceptable toxicity to compounds of Formula I.

The new compounds of general formula I and their salts are used therapeutically mainly orally or rectally. They can also be administered, however, parenterally in the form of aqueous dispersions produced with the aid of solubility promoters and/or emulsifying agents or in the form of aqueous solutions of their pharmacologically acceptable salts.

Compounds of the general formula I, in particular those having a hydrogen atom as R₂ or hydroxyl or amino groups as substitutents of R₁ or R₂, can also be used as intermediate products, for example, for the production of other pharmacologically valuable substances.

In the compounds of general formula I and in the corresponding starting materials, R₁ is, for example, methyl, ethyl, propyl, isopropyl, butyl, isobutyl, cyclopentyl, cyclohexyl, cyclohexenyl, cyclohexylmethyl, 2,5-endomethylenecyclohexylmethyl, benzyl, β-phenylethyl, phenyl, o-, m- and p-tolyl, 2,3-, 2,4-, 3,4-, 2,5- or 2,6- xylyl, o-, m- and p-ethylphenyl, p-propylphenyl, p-isopropylphenyl, p-butylphenyl, p-isobutylphenyl, p-tert. butylphenyl, α-phenyl-p-tolyl (p-benzylphenyl), p-biphenylyl, o-, m- and p-fluorophenyl, o-, m- and p-chlorophenyl, o-, m- and p-bromophenyl, 2,4-dichlorophenyl, 2,5-dichlorophenyl, 3,4-dichlorophenyl, 2-methyl-4-chlorophenyl, 2-methyl-5-chlorophenyl, α,α,α-trifluoro-m-tolyl, α,α,α-trifluoro-p-tolyl, 2,4,6-trimethylphenyl, m-methoxyphenyl, p-methoxyphenyl, m-ethoxyphenyl, p-ethoxyphenyl, p-methylthiophenyl, o-hydroxyphenyl, m- hydroxphenyl, p-hydroxyphenyl, 2-hydroxy-4-methylphenyl, 2- hydroxy-5-methylphenyl, p-methylsulphonylphenyl, p-acetamidophenyl, m-acetamidophenyl, m-aminophenyl, m-nitrophenyl, 3-acetamido-4-chlorophenyl, 3-amino-4-chlorphenyl, 2-hydroxy-4-chlorophenyl, 2-hydroxy-5-chlorophenyl, 2-hydroxy-5-methoxyphenyl, 3-sulfamyl -4-chlorophenyl, m-dimethylsulfamylphenyl, 3-nitro-4-aminophenyl, 3-nitro-4-methylthiophenyl, 1-naphthyl, 2-naphthyl, 2-thienyl.

A is, for example, ethylene, trimethylene, tetramethylene, phenylethylene, 2,2-dimethyltrimethylene, 1,2-diphenyltrimethylene, o-phenylene, 4-methyl-o-phenylene, 3-chloro-o-phenylene, 4-chloro-o-phenylene, 3,6-dichloro-o-phenylene, 3,4,5,6-tetrachloro-o-phenylene, 4-methoxy-o-phenylene, cis-1,2-cyclohexylene, or a vicinal divalent pyridine radical.

B is, for example, ethylene, trimethylene, tetramethylene, 2,2-dimethyltrimethylene, methylethylene, 1,1-dimethylethylene, 1,2-dimethylethylene, ethylethylene, o-benzylene, α,α'-o-xylylene, o-phenylene, 4-methyl-o-phenylene, 3-chloro-o-phenylene, 4-chloro-o-phenylene, 4-methoxy-o-phenylene, 1,2-naphthylene, 1,8-naphthylene, o,o'-biphenylene, cis- or trans- 1,2-cyclohexylene or a vicinal divalent pyridine radical.

The divalent radicals listed under A and B which are non-symmetrical can actually be in any of the various possible arrangements in the molecule of the end product.

$R_2$ is, for example, hydrogen, methyl, ethyl, propyl, isopropyl, butyl, isobutyl, 2-hydroxyethyl, 3-hydroxypropyl, 2-methoxyethyl, 2-ethoxyethyl, 3-methoxypropyl, 2-methylthioethyl, 3-methylthiopropyl, 2-aminoethyl, 2-ethylaminoethyl, 2-dimethylaminoethyl, 2-diethylaminoethyl, 3-dimethylaminopropyl, 3-diethylaminopropyl, benzyl, p-dimethylaminobenzyl, p-chlorobenzyl, m-trifluoromethylbenzyl, veratryl, β-phenylethyl, α-methyl-β-phenylethyl, β-(1-pyrrolidinyl)-ethyl, β-piperidinoethyl, β-hexamethyleneiminoethyl, β-morpholinoethyl, β-thiomorpholinoethyl, β-(1-piperazinyl)-ethyl or β-(4-methyl-1-piperazinyl)-ethyl.

Many of the compounds of general formulae II, III and IV used as starting materials are known or can be produced by generally known processes. In the starting materials of the general formula II, the carbonyl group, as defined, is always bound, at least unilaterally, to a benzene ring or to a heteroaromatic ring, i.e. to a thiophene or pyridine ring. In the most simple case, when in the starting material of general formula II or III, A is an aliphatic radical and $R_1$ is an aromatic or heteroaromatic radical and, in the starting material of general formula/IV, B is an aliphatic radical, products are obtained by the process which have two fused rings and a further ring bound at an angle. If A and/or B is a cyclic radical, then ring systems are formed which have 3, 4 or more condensed rings. As defined, only two of the carbon atoms between the two valences of A and B can belong of the same ring. Others, however, can be outside the ring or can belong to a second ring such as is the case, e.g., in condensation products which o-phenacylbenzoic acid of general formula II or α,2-toluenediamine (o-aminobenzylamine) or 1,8-naphthalenediamine or 2,2 '-biphenyldiamine of general formula IV is used as starting material. The following compounds are given as examples of starting materials of the general formulae II and III:

o-acetylbenzoic acid, o-propionylbenzoic acid, o-butyroylbenzoic acid, 3-benzoylpropionic acid, 3-(m-fluorobenzoyl)-propionic acid, 3-(p-fluorobenzoyl)-propionic acid, 3-(m-chlorobenzoyl)-propionic acid, 3-(p-chlorobenzoyl)-propionic acid, 3-(p-bromobenzoyl)-propionic acid, 3-(m-nitrobenzoyl)-propionic acid, 3-(m-toluoyl-propionic acid, 3-(p-toluoyl)-propionic acid, 3-(p-ethylbenzoyl)-propionic acid, 3-(p-isopropylbenzoyl)-propionic acid, 3-(p-tert.butylbenzoyl)-propionic acid, 3-(α,α,60 -trifluoro-m-toluoyl)-propionic acid, 3-salicyloylpropionic acid, 3-(m-hydroxybenzoyl)-propionic acid, 3-(p-anisoyl)-propionic acid, 2-butylthio-3-benzoyl-propionic acid, 2-butyl-3-(p-chlorobenzoyl)-propionic acid, 2-phenylthio-3-benzoyl-propionic acid, 2-phenyl-3-benzoyl-propionic acid, 2-phenyl-3-(p-anisoyl)-propionic acid, 4-benzoyl-butyric acid, 3,3-dimethyl-4-benzoyl-butyric acid, 3,3-dimethyl-4-(p-chlorobenzoyl)-butyric acid, 2,3-diphenyl-3-benzoyl-butyric acid, 2,3-diphenyl-4-(p-anisoyl)-butyric acid, 3-(2'-thenoyl)-propionic acid, 2-phenyl-3-(2'-thenoyl)-propionic acid, 4-(2'-thenoyl)-butyric acid, 5-benzoyl-valeric acid, 2-benzoyl-cyclohexanecarboxylic acid, o-benzoyl-benzoic acid, o-(m'-fluorobenzoyl)-benzoic acid, o-(p'-fluorobenzoyl)-benzoic acid, o-(m'-chlorobenzoyl)-benxoic acid, o-(p'-chlorobenzoyl)-benzoic acid, o-(p'-bromobenzoyl)-benzoic acid, o-(m'-nitrobenzoyl)-benzoic acid, o-(m'-toluoyl)-benzoic acid, o-(p'-toluoyl)-benzoic acid, o-(p'-ethylbenzoyl)-benzoic acid, o-(p'-isopropylbenzoyl)-benzoic acid, o-(p'-tert. butylbenzoyl)-benzoic acid, o-(α,α,α-trifluoro-m'-toluoyl)-benzoic acid, o-(α,α,α-trifluoro-p'-toluoyl)-benzoic acid, o-salicyloyl-benzoic acid, o-(m'-hydroxybenzoyl)-benzoic acid, o-(p'-hydroxybenzoyl)-benzoic acid, o-(m'-anisoyl)-benzoic acid, o-(p'-anisoyl)-benzoic acid, o-(p'-ethoxybenzoyl)-benzoic acid, o-(p'-methylthiobenzoyl)-benzoic acid, o-(p'-methyl-sulfonylbenzoyl)-benzoic acid, o-(m'-aminobenzoyl)-benzoic acid, o-(m'-acetamidobenzoyl)-benzoic acid, o-(p'-acetamidobenzoyl)-benzoic acid, o-(m'-dimethylsulphamylbenzoyl)-benzoic acid, o-(3,4-dichlorobenzoyl)-benzoic acid, o-(2,4-dimethylbenzoyl)-benzoic acid, o-(2,5-dimethylbenzoyl)-benzoic acid, o-(3,4-dimethylbenzoyl)-benzoic acid, o-(5-chlorosalicyloyl)-benzoic acid, o-(3-nitro-4-hydroxybenzoyl)-benzoic acid, o-(2-hydroxy-5-methylbenzoyl)-benzoic acid, o-(2-hydroxy-5-methoxybenzoyl)-benzoic acid, o-(3-nitro-4-methylthiobenzoyl)-benzoic acid, o-(3-amino-4-chlorobenzoyl)-benzoic acid, o-(3-nitro-4-aminobenzoyl)-benzoic acid, o-(3-acetamido-4-chlorobenzoyl)-benzoic acid, o-(3- sulfamyl)-4-chlorobenzoyl-benzoic acid, o-(2,4,6-trimethylbenzoyl)-benzoic acid, 2-benzoyl-3-chlorobenzoic acid, 2-benzoyl-3-nitrobenzoic acid, 2-benzoyl-3,4,5,6-tetrachlorobenzoic acid, 2-(p-chlorobenzoyl)-3-chlorobenzoic acid, 2-(p-chlorobenzoyl)-3,4,5,6-tetrachlorobenzoic acid, 2-(p-phenylbenzoyl)-benzoic acid, o-(2-naphthoyl)-benzoic acid, o-phenylacetylbenzoic acid, o-phenacylbenzoic acid, o-benzoylphenylacetic acid, 3-(p-chlorobenzoyl)-picolinic acid, 3-benzoylpropionic acid ethyl ester, o-benzoylbenzoic acid methyl ester, 3-chloro-3-phenylphthalide, 3-methoxy-3-phenylphthalide, 3-acetoxy-3-phenylphthalide.

As starting materials of general formula IV can be mentioned:

ethylenediamine, N-methylethylenediamine, N-ethylethylenediamine, N-propylethylenediamine, N-isopropylethylenediamine, N-butylethylenediamine, N-(2-hydroxyethyl)-ethylenediamine, diethylenetriamine, 1,1-dimethyldiethylenetriamine (N,N-dimethyldiethylenetriamine), 1,2-propanediamine, 1,2-butanediamine, 2,3-butanediamine, $N^2$-isopropyl-2-methyl-1,2-propanediamine, cis-1,2-cyclohexanediamine, trans-1,2- cyclohexanediamine, o-phenylenediamine, N-methyl-o-phenylenediamine, N-ethyl-o-phenylenediamine, N-(2-dimethylaminoethyl)-o-phenylenediamine, N-(2-diethylaminoethyl)-o-phenylenediamine, toluene-3,4-diamine (4-methyl-o-phenylenediamine), 2,3-pyridinediamine, 1,3-propanediamine, N-methyl-1,3-propanediamine, N-ethyl-1,3-propanediamine, N-propyl-1,3-propanediamine, N-isopropyl-1,3-propanediamine, N-butyl-1,3-propanediamine, 1,3-diamino-2-propanol, 2-methyl-1,3-propanediamine, 1,3-butanediamine, 2,4-pentanediamine, toluene-α,2-diamine (o-aminobenzylamine), 1,8-naphthalenediamine, 1,4-butanediamine, N-methyl-1,4-butanediamine, N-ethyl-1,4-butanediamine, 2,2'-biphenyldiamine.

To produce compounds according to the invention, an amine of general formula IV is reacted at temperatures of about 100°–250° in the presence or absence of a solvent such as, e.g. toluene, chlorobenzene, xylene, o-chlorotoluene, o-dichlorobenzene, nitrobenzene, amyl alcohol, with a ketocarboxylic acid or a derivative thereof corresponding to the general formulae II and/or III. The condensation according to the invention is performed while splitting off the equimolar amount of the compound H-X and water and can optionally be promoted by agents splitting off water such as, e.g. zinc chloride, or by distilling off the reaction water or the liberated alkanol or the liberated acetic acid.

In many cases, two reaction steps can be observed in the performance of the process according to the invention. First, an intermediate product of the general formula V

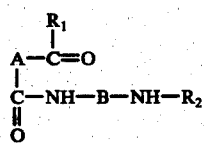
(V)

which, in some cases, is wholly or partially in the tautomeric form corresponding to general formula VI

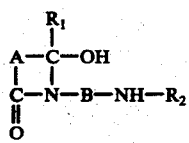
(VI)

in which formulae $R_1$, $R_2$, A and B have the meanings given in general formula I, is formed whilst a compound X—H, i.e. water, hydrogen halide, low alkanol or low alkanoic acid is split off. The end product of general formula I is then formed therefrom by splitting off water under the reaction conditions given above. Thus, the present invention also embraces the production of these end products from intermediate products of the general formulae V and/or VI. This process is characterised by subjecting compounds of these general formulae to conditions which split off water, most simply by heating in a solvent which azeotropically distills off with water such as, e.g. chlorobenzene or o-dichlorobenzene, or heating in the presence of an agent which splits off water such as, e.g. zinc chloride, magnesium perchlorate or phosphorous pentoxide.

Preferred antiinflammatory agents according to the invention are those falling under the formula

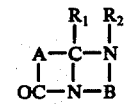

wherein $R_1$ is a member selected from the group consisting of lower alkyl, benzyl, naphthyl and phenyl substituted by the following: hydrogen, lower alkyl, lower alkoxy, lower alkyl-thio, lower alkyl-sulfonyl, lower alkyl-amino, lower alkanoyl-amino, N-lower alkyl-substituted sulfamyl, hydroxyl, nitro, amino, sulfamyl, trifluoromethyl, chlorine, bromine, fluorine, $R_2$ is a member selected from the group consisting of hydrogen, lower alkyl, hydroxy-lower alkyl, lower alkoxy-lower alkyl, lower alkylthio-lower alkyl, amino-lower alkyl, N-lower alkyl-substituted amino-lower alkyl, polymethylenimino-lower alkyl with from 5 to 7 ring members, lower alkyl-substituted polymethylenimino-lower alkyl with from 5 to 7 ring members, 4-lower alkyl-piperazino, morpholino and thiomorpholino, A represents a member selected from the group consisting of straight-chain alkylene of from 2 to 3 carbon atoms, the aforesaid alkylene substituted with lower alkyl, the aforesaid alkylene substituted with phenyl, o-phenylene, o-cyclohexylene and pyridylene the free linkages of which are at adjacent carbon atoms thereof, and B represents a member selected from the group consisting of straight-chain alkylene of from 2 to 4 carbon atoms, the last-mentioned alkylene substituted with lower alkyl, o-phenylene, pyridylene, naphtylene and diphenylene, the free linkages of the three last-mentioned members being separated from each other by not more than two carbon atoms in the case of said linkages being at one and the same ring of the member, and a pharmaceutically acceptable salt of said compound with an acid as defined hereinbefore.

The following non-limitation examples further illustrate the invention. The temperatures are given therein in degrees Centigrade. Parts and percentages are given by weight unless stated otherwise, and the relationship of parts by weight to parts by volume is as that of grams to milliliters. "Torr" stands for "mm Hg".

EXAMPLE 1

22.6 Parts of o-benzoyl-benzoic acid are added to 7.2 parts of ethylenediamine. A thick slurry is formed whilst the temperature rises to about 80°. The temperature is gradually raised to 140° and, at the same time, the excess ethylenediamine and the reaction water are distilled off. After heating for another 2 hours at 140°, the melt, which has become clear, is poured into a bowl and, after it has cooled, it is rubbed with a little benzene. The crude product separates out in the form of colourless crystals. After recrystallising once from benzene, pure 9b-phenyl-1,2,3,9b-tetrahydro-5H-imidazo[2,1-a]isoindole-5-one of the formula

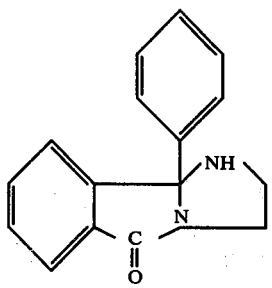

is obtained., M.P. 150°–151°.

To produce the hydrochloride, the above reaction product is added, for example to about 20% hydrochloric acid and the precipitated hydrochloride is filtered off. The reaction product however, can be dissolved in ethanol and the hydrochloride precipitated by introducing hydrogen chloride. The hydrochloride can be purified, e.g., by recrystallisation from ethanol. It decomposes on heating at 240°–260° and easily dissolves in water.

On using correspondingly varied starting materials, the following compounds are obtained by the same process:

a)     9b-(p-chlorophenyl)-1,2,3,9b-tetrahydro-5H-imidazo[2,1-a]isoindol-5-one, M.P. 166°–168°;

b)     4b-(p-chlorophenyl)-4b,5-dihydro-11H-isoindolo[2,1-a]benzimidazol-11-one, M.P. 158°–160°;

c)     9b-(p-methylthiophenyl)-1,2,3,9b-tetrahydro-5H-imidazo[2,1-a] isoindol-5-one, M.P. 147°;

d)     1-methyl-9b-(p-chlorophenyl)-1,2,3,9b-tetrahydro-5H-imidazo[2,1-a]isoindol-5-one, M.P. 135°–137°;

e)     1-butyl-9b-(p-chlorophenyl)-1,2,3,9b-tetrahydro-5H-imidazo [2,1-a]isoindol-5-one, M.P. 121°–123°;

f)     9b-(2'-hydroxy-5'-chlorophenyl)-1,2,3,9b-tetrahydro-5H-imidazo]2,1-a]isoindol-5-one, M.P. 258°–260°;

g)     9b-(p-methylsulphonylphenyl)-1,2,3,9b-tetrahydro-5H-imidazo[2,1-a]isoindol-5-one, M.P. 265°–267°;

h)     2-methyl-9b-(p-chlorophenyl)-1,2,3,9b-tetrahydro-5H-imidazo[2,1-a]isoindol-5-one (The two stereoisomers which melt at 153.5°–155° and 195.5°–198°, are obtained by chromatographic separation in an aluminum oxide column with chloroform);

i)     10b-phenyl-10b,11-dihydro-6H-pyrido[2',3'-4,5]imidazo[2,1-a]isoindol-6-one, M.P. 213°–215°;

k)     9b-(α,α,α-trifluoro-p-tolyl)-1,2,3,9b-tetrahydro-5H-imidazo[2,1-a]isoindol-5-one, M.P. 191°–191.5°;

l)     9b-(p-bromophenyl)-1,2,3,9b-tetrahydro-5H-imidazo[2,1-a]isoindol-5-one, M.P. 146°–148°;

m)     9b-(p-methoxyphenyl)-1,2,3,9b-tetrahydro-5H-imidazo[2,1-a]isoindol-5-one, M.P. 160°–161°;

n)     9b-(3'-amino-4'-chlorophenyl)-1,2,3,9b-tetrahydro-5H-imidazo [2,1-a]isoindol-5-one, M.P. 175°–176°;

o)     9b-(1'-naphthyl)-1,2,3,9b-tetrahydro-5H-imidazo[2,1-a]isoindol-5-one, M.P. 166°–167°;

p)     9b-(3'-acetamido-4'-chlorophenyl)-1,2,3,9b-tetrahydro-5H-imidazo[2,1-a]isoindol-5-one, M.P. 198°–199°;

q)     4b-phenyl-5-(2'-diethylaminoethyl)-4b,5-dihydro-11H-isoindolo [2,1-a]benzimidazol-11-one of the formula

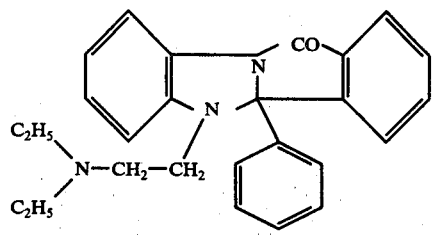

M.P. 121°–122.5°;

r)     1(2'-dimethylaminoethyl)-9b-phenyl-1,2,3,9b-tetrahydro-5H-imidazo[2,1-a]isoindol-5-one (citrate), M.P. 179°–181°, and s)     1-(3'-dimethylaminopropyl)-9b-phenyl-1,2,3,9b-tetrahydro-5H-imidazo[2,1-a]isoindol-5-one, M.P. 100°–101°.

t)     4b-phenyl-5-(β-aminoethyl)-4b,5-dihydro-11H-isoindolo [2,1-a]benzimidazol-11-one.

u)     9b-(m-sulfophenyl)-1,2,3,9b-tetrahydro-5H-imidazo[2,1-a] isoindol-5-one.

EXAMPLE 2

22.6 Parts of o-benzoyl-benzoic acid are dissolved in 100 ml of chlorobenzene. 7.4 Parts of N-methylethylenediamine are added within 10 minutes. The temperature is then raised within 1 - 2 hours to such an extent that some chlorobenzene is continuously distilled off with the reaction water until the boiling point of the pure chlorobenzene (130°–132°) is attained. 80–90% of the theoretical amount of reaction water can be removed from the distillate. The remainder of the chlorobenzene is distilled off from the reaction mass in vacuo and the viscous oil which remains is crystallised by the addition of about 10 parts of ethyl acetate. The 1-methyl-9b-phenyl-1,2,3,9b-tetrahydro-5H-imidazo[2,1-a]isoindol-5-one so obtained of the formula

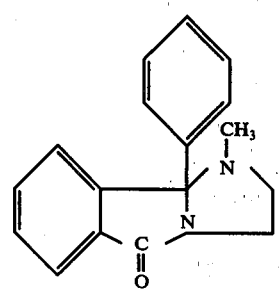

is filtered off and recrystallised from a mixture of 30 parts of ethyl acetate and 30 parts of petroleum ether (B.P. 30°–60° ). M.P. 120°–122°.

The following compounds are obtained by the same process on using correspondingly varied starting materials:

a)     1-ethyl-9b-phenyl-1,2,3,9b-tetrahydro-5H-imidazo[2,1-a]isoindol-5-one, M.P. 119°–121°;

b)     1-propyl-9b-phenyl-1,2,3,9b-tetrahydro-5H-imidazo[2,1-a]isoindol-5-one, M.P. 134°–136°;

c)     9b-(p-tolyl)-1,2,3,9b-tetrahydro-5H-imidazo[2,1-a]isoindol-5-one, M.P. 152°–154°;

d)     1-methyl-9b-(p-tolyl)-1,2,3,9b-tetrahydro-5H-imidazo[2,1-a]isoindol-5-one, M.P. 112°–114°;

e) 9b-(p-ethylphenyl)-1,2,3,9b-tetrahydro-5H-imidazo[2,1-a]isoindol-5-one, M.P. 119°-124°;

f) 1-methyl-9b-(m-nitrophenyl)-1,2,3,9b-tetrahydro-5H-imidazo [2,1-a]isoindol-5-one, M.P. 148°-150°;

g) 9b-(m-nitrophenyl)-1,2,3,9b-tetrahydro-5H-imidazo[2,1-a]isoindol-5-one, M.P. 169°-171°;

h) 9b-(p-fluorophenyl)-1,2,3,9b-tetrahydro-5H-imidazo[2,1-a]isoindol-5-one, M.P. 188°-190°, and i) 4b-phenyl-5-methyl-4b,5-dihydro-11H-isoindolo[2,1-a]benzimidazol-11-one of the formula

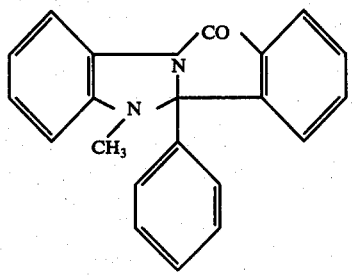

M.P. 154°-156°.

j) 1-(β-hydroxyethyl)-9b-phenyl-1,2,3,9b-tetrahydro-5H-imidazo[2,1-a]isoindol -5-one;

k) 1-(β-methoxyethyl)-1,2,3,9b-tetrahydro-5H-imidazo[2,1-a]isoindol -5-one;

l) 1-(β-methylthioethyl)-1,2,3,9b-tetrahydro-5H-imidazo[2,1-a]isoindol -5-one;

m) 1-(β-piperidino-ethyl)-1,2,3,9b-tetrahydro-5H-imidazo [2,1-a]isoindol -5-one;

n) 1-(β-pyrrolidino-ethyl)-1,2,3,9b-tetrahydro-5H-imidazo [2,1-a]isoindol -5-one;

o) 1-(β-2',6'-dimethylpiperidino-ethyl)-1,2,3,9b-tetrahydro-5H-imidazo[2,1-a]isoindol -5-one;

p) 1-(β-4'-methylpiperazinyl-ethyl)-1,2,3,9b-tetrahydro-5H-imidazo[2,3-a]isoindol -5-one;

q) 1-(β-morpholino-ethyl)-1,2,3,9b-tetrahydro-5H-imidazo [2,1-a]isoindol -5-one;

r) 1-(β-thiomorpholino)-1,2,3,9b-tetrahydro-5H-imidazo[2,1-a]isoindol -5-one.

EXAMPLE 3

25.6 Parts of o-(p'-anisoyl)-benzoic acid, 50 parts by volume of o-chlorotoluene and 8,8 parts of N-ethylethylenediamine are mixed and the mixture is heated within one hour in such a way that the reaction water and o-chlorotoluene are slowly distilled off together. By the time the boiling point of the pure solvent (159°) has been reached, 3.5 parts of water have been distilled off. The remaining chlorotoluene is distilled off in vacuo and the viscous residue is distilled under high vacuum. The greenish destillate which passes over at 185°-187° under about 0.01 Torr. is rubbed with a little ethyl acetate and so brought to crystallisation. On recrystallising from ethyl acetate, the pure 1-ethyl-9b-(p-methoxyphenyl)-1,2,3,9b-tetrahydro-5H-imidazo[2,1-a]isoindol -5-one is formed of the formula

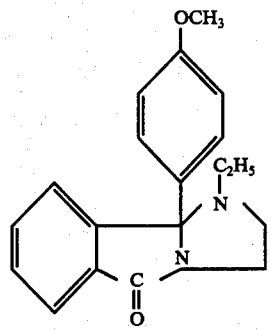

M.P. 76°-78°.

On using corresponding varied starting materials, the following compounds are obtained by the same process:

a) 1-ethyl-9b-(p-chlorophenyl)-1,2,3,9b-tetrahydro-5H-imidazo [2,1-a]isoindol -5-one, M.P. 114°-116°;

b) 9b-(2',4'-xylyl)-1,2,3,9b-tetrahydro-5H-imidazo[2,1-a]isoindol -5-one, M.P. 177.5°-179°;

c) 1-methyl-9b-(p-methoxyphenyl)-1,2,3,9b-tetrahydro-5H-imidazo[2,1-a]isoindol -5-one, M.P. 107°-109°;

d) 1-propyl-9b-(p-chlorophenyl)-1,2,3,9b-tetrahydro-5H-imidazo[2,1-a]isoindol -5-one, M.P. 137°-140°;

e) 1-methyl-9b-(p-ethylphenyl)-1,2,3,9b-tetrahydro-5H-imidazo[2,1-a]isoindol -5-one, M.P. 105°-109°;

f) 1-ethyl-9b-(p-tolyl)-1,2,3,9b-tetrahydro-5H-imidazo[2,1-a]isoindol -5-one, M.P. 109°-111°, and g) 1-ethyl-9b-(p-ethylphenyl)-1,2,3,9b-tetrahydro-5H-imidazo [2,1-a]isoindol -5-one, amorphous, B.P.169°-178°/0.005 Torr.

EXAMPLE 4

22.6 Parts of o-benzoyl-benzoic acid and 50 parts by volume of chlorobenzene and 10.2 parts of N-isopropyl-ethylenediamine are heated to 130° within 30-40 minutes, whereby finally only chlorobenzene is distilled off. 1.8 parts of water are obtained in this way. On cooling the solution, the intermediate product crystallises out, i.e. 2-(2'-isopropylaminoethyl)-3-hydroxy-3-phenyl-1-isoindolinone (2-(2'-isopropylaminoethyl)-3-hydroxy-3-phenyl-phthalimidine), M.P. 242°-243°.

This intermediate product is further condensed by heating for 10 minutes at 245°-250°, whereby reaction water is developed. After cooling and rubbing with ethyl acetate, the 1-isopropyl-9b-phenyl-1,2,3,9b-tetrahydro-5H-imidazo[2,1-a]isoindol -5-one of the formula

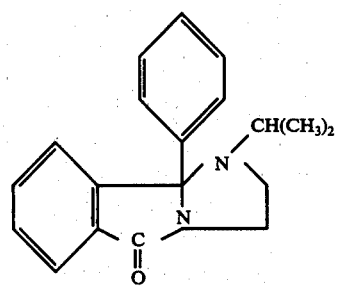

crystallises. After recrystallisation from ethyl acetate and petroleum ether (B.P. 30°-60°), it melts at 178°-180°.

EXAMPLE 5

27.4 Parts of 3-(p-chlorophenyl)-3-methoxy-phthalide are added within 1 hour at 80° to a mixture of 50 parts by volume of ethylene diamine and 10 parts of water. After 2 hours, the reaction mixture is diluted with water up to 500 parts by volume and the liquid is decanted from the intermediate product which crystallises out. In this way, 2-(2'-aminoethyl)-3-hydroxy-3-(chlorophenyl)-1-isoindolinone (2-(2'-aminoethyl)-3-hydroxy-3-(p-chlorophenyl)-phthalimidine) is obtained, M.P. 172°–174°. On melting, water is split off and 9b-(p-chlorophenyl)-1,2,3,9b-tetrahydro-5H-imidazo[2,1-a]isoindol -5-one is obtained of the formula

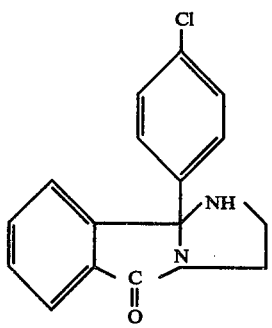

which melts at 166°–168° (see Example 1a).

EXAMPLE 6

22.6 Parts of o-benzoyl-benzoic acid and 8.9 parts of 1,3-propanediamine are heated within 1 hour to 140° and this temperature is maintained for 1 hour. The melt is then cooled and afterwards dissolved in 300 parts by volume of ethyl acetate, the hot solution is filtered with decolourising charcoal and left to stand whereupon 10b-phenyl-1,3,4,10b-tetrahydro-pyrimido[2,1-a]isoindol -6(2H)-one of the formula

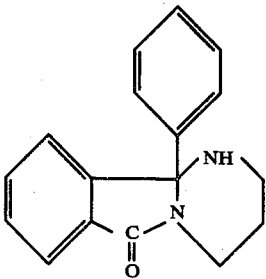

crystallises out. M.P. 176°–177°.

The following compounds are obtained by the same process on using correspondingly varied starting materials:

a) 10b-(p-chlorophenyl)-1,3,4,10b-tetrahydro-pyrimido[2,1-a]isoindol -6(2H)-one, M.P. 159°–160°;
b) 10b-(m-nitrophenyl)-1,3,4,10b-tetrahydro-pyrimido[2,1-a]isoindol -6(2H)-one, M.P. 176.5°–178°;
c) 10b-(p-methoxyphenyl)-1,3,4,10b-tetrahydro-pyrimido[2,1-a]isoindol -6(2H)-one, M.P. 161.5°–163°;
d) 10b-(p-methylthiophenyl)-1,3,4,10b-tetrahydro-pyrimido [2,1-a]isoindol -6(2H)-one, M.P. 163°–164°;
e) 10b-(p-ethoxyphenyl)-1,3,4,10b-tetrahydro-pyrimido[2,1-a]isoindol -6(2H)-one, M.P. 166°–167°;
f) 10b-(3'-amino-4'-chlorophenyl)-1,3,4,10b-tetrahydropyrimido[2,1-a]isoindol -6(2H)-one, M.P. 168°–169°;
g) 10b-(2'-hydroxy-5'-methylphenyl)-1,3,4,10b-tetrahydropyrimido[2,1-a]isoindol -6(2H)-one, M.P. 257°–259°;
h) 10b-(p-bromophenyl)-1,3,4,10b-tetrahydro-pyrimido[2,1-a]isoindol -6(2H)-one, M.P. 151°–152°;
i) 10b-(p-fluorophenyl)-1,3,4,10b-tetrahydro-pyrimido[2,1-a]isoindol -6(2H)-one, M.P. 143°–146°, and
j) 7a-phenyl-7,7a-dihydro-12H-isoindolo[2,1-a]perimidin -12-one of the formula

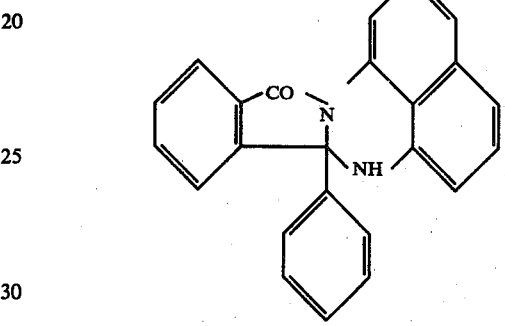

M.P. 252°–254°.

EXAMPLE 7

22.6 Parts of o-benzoyl-benzoic acid are slurried in 50 parts by volume of chlorobenzene and 8.8 parts of N-methyl-1,3-propanediamine are added. The reaction mixture is heated while slowly distilling off reaction water and chlorobenzene until, after 1½ hours, the boiling point of the pure chlorobenzene has been attained. 3.5 Parts of water are so distilled off. After cooling the chlorobenzene solution, petroleum ether (B.P. 30°–60°) is added until the solution begins to turn cloudy whereupon 1-methyl-10b-phenyl-1,3,4,10b-tetrahydropyrimido[2,1-a]isoindol -6(2H)-one of the formula

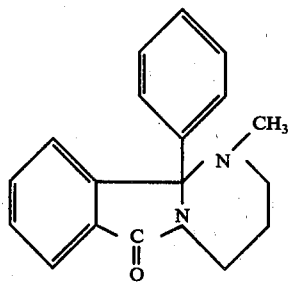

crystallises out. After recrystallising from ethyl acetate, it melts at 169°–171°.

Using correspondingly varied starting materials, the following compounds are obtained by the same process:

a) 1-methyl-10b-(p-chlorophenyl)-1,3,4,10b-tetrahydro-pyrimido [2,1-a]isoindol -6(2H)-one, M.P. 142°–144°, and b) 1-methyl-10b-(m-nitrophenyl)-1,3,4,10b-tetrahydro-pyrimido [2,1-a]isoindol-6(2H)-one, M.P. 166°-168°.

c) 1-methyl-10b-(m-aminophenyl)-1,3,4,10b-tetrahydropyrimido[2,1-a]isoindol-6(2H)-one;

d) 1-methyl-10b-(m-N,N-dimethylamino-phenyl)-1,3,4,10b-tetrahydro-pyrimido[2,1-a]isoindol-6(2H)-one; the starting compound, o-(m-N,N-dimethylamino-benzoyl)-benzoic acid is produced from the corresponding aminobenzoyl benzoic acid by conventional alkylation.

EXAMPLE 8

25.6 Parts of o-(p'-anisoyl)-benzoic acid are heated within 2 hours to 159° with 8.8 parts of N-methyl-1,3-propanediamine and 50 parts by volume of o-chlorotoluene, whereby the reaction water and chlorotoluene slowly distill off. After evaporating off the chlorotoluene, the amorphous crude product is distilled under high vacuum. The destillate which passes over at 213° under 0.03 Torr. is recrystallised from ethyl acetate. In this way, pure 1-methyl-10b-(p-methoxyphenyl)-1,3,4,10b-tetrahydro-pyrimido[2,1-a]isoindole-6(2H)-one is obtained of the formula

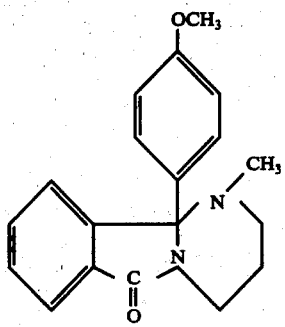

M.P. 128°-131°.

On using correspondingly varied starting materials, the following compounds are obtained by the same process:

a) 1-ethyl-10b-(p-chlorophenyl)-1,3,4,10b-tetrahydropyrimido [2,1-a]isoindol-6(2H)-one, amorphous, B.P.200°-202°/0.04 Torr;

b) 1-propyl-10b-(p-chlorophenyl)-1,3,4,10b-tetrahydropyrimido [2,1-a]isoindole-6(2H)-one, amorphous, B.P.198°-200°/0.02 Torr, and c) 1-ethyl-10b-(p-methoxyphenyl)-1,3,4,10b-tetrahydropyrimido [2,1-a]isoindol-6(2H)-one, M.P. 126°-129°.

EXAMPLE 9

22.6 Parts of o-benzoyl-benzoic acid and 11.6 parts of N-propyl-1,3-propanediamine are haeted within 1½ hours with 50 parts by volume of o-dichlorobenzene until the boiling point of the latter is attained. Almost the theoretical amount of reaction water is azeotropically distilled off. The clear solution is evaporated to dryness in vacuo, the oily residue is dissolved in ethyl acetate and crystallised by the dropwise addition of pentane. In this way, 1-propyl-10b-phenyl-1,3,4,10b-tetrahydro-pyrimido[2,1-a]isoindol-6(2H)-one is obtained of the formula

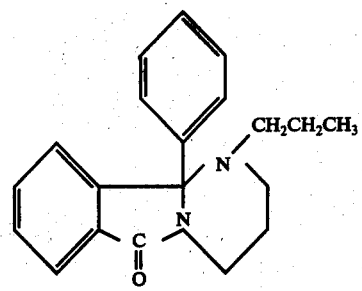

M.P. 135°-137°. 1-Ethyl-10b-phenyl-1,3,4,10b-tetrahydro-pyrimido[2,1-a]isoindol -6(2H)-one is obtained in the same manner from o-benzoyl-benzoic acid and N-ethyl-1,3-propanediamine. M.P. 131°-133°.

EXAMPLE 10

34.0 Parts of o-(3-sulphamoyl-4-chlorobenzoyl)-benzoic acid are dissolved in 150 parts by volume of n-amyl alcohol. 7.5 Parts of 1,3-propanediamine are added dropwise and then the whole is distilled slowly until the boiling point of the pure amyl alcohol (136.5°) is attained. 3.4 Parts of water are distilled off simultaneously. The clear solution is allowed to cool whereupon the 10b-(3'-sulphamoyl-4'-chlorophenyl)-1,3,4,10b-tetrahydro-pyrimido[2,1-a]isoindol -6(2H)-one of the formula

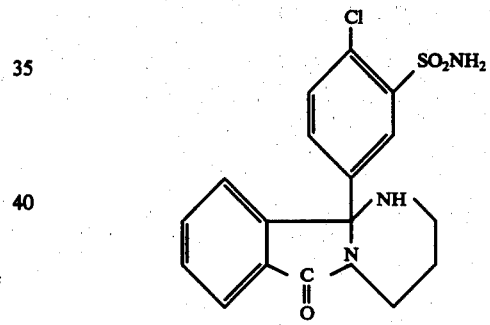

crystallises out. After recrystallising from methanol, it melts at 222°-224°.

When using the correspondingly varied starting benzoic acid, the following compound is obtained by the same process:

(a) 10b-(3'-N,N-dimethyl-sulfamyl-4'-chlorophenyl)-1,3,4,10b-tetrahydro-pyrimido[2,1-a]isoindol- 6(2H)-one.

EXAMPLE 11

22.6 Parts of o-benzoyl-benzoic acid and 10.1 parts of 1,4-butanediamine in 100 parts by volume of o-dichlorobenzene are heated within 2 hours to 179° whereby reaction water and a little dichlorobenzene azeotropically distill off. The solvent is then distilled off in vacuo whereupon an oil remains which spontaneously crystallises after some time. On recrystallising from benzene, the pure 11b-phenyl-1,2,3,4,5,11b-hexahydro-7H-[1,3]-diazepino[2,1-a]isoindol-7-one is obtained of the formula

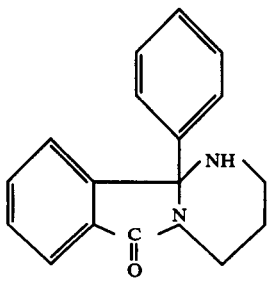

It melts at 180°–181°. On using o-(p'-chlorobenzoyl)-benzoic acid, 11b-(p-chlorophenyl)-1,2,3,4,5,11b-hexahydro-7H-[1,3]diazepino[2,1-a]isoindol-7-one is obtained in the same manner. It melts at 134°–135°.

EXAMPLE 12

26.1 Parts of o-(p-chlorobenzoyl)-benzoic acid and 19.3 parts of 2,2'-biphenyldiamine (o,o-diaminobiphenyl) are heated to 160° and this temperature is maintained for 2 hours. After cooling, the crude product is recrystallised from chlorobenzene. In this way, the pure 9a-(p-chlorophenyl)-9,9a-dihydro-14H-dibenzo[4,5,6,7][1,3]diazepino[2,1-a]isoindol-14-one is obtained of the formula

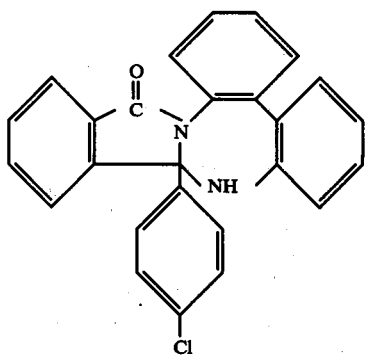

M.P. 321°–323°.

EXAMPLE 13

26.2 Parts of 3-(p-chlorobenzoyl)-picolinic acid and 9.0 parts of 1,3-propanediamine are heated to 160° and this temperature is maintained for 1½ hours. After cooling, the crude product is recrystallised twice from ethyl acetate. In this way, the pure 10b-(p-chlorophenyl)-1,3,4,10b-tetrahydro-pyrido[3',2'-3,4]pyrrolo [1,2-a]pyrimidin-6(2H)-one is obtained of the formula

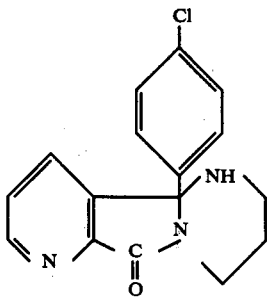

M.P. 246°–247°. In the same way, on using ethylenediamine instead of 1,3-propanediamine, 9b-(p-chlorophenyl)-1,2,3,9b-tetrahydro-5H-imidazo[1',2'-1,2]pyrrolo[4,3-b]pyridine-5-one is obtained of the formula

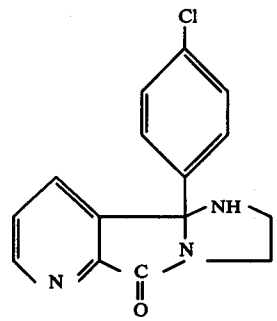

M.P. 226°–227°.

EXAMPLE 14

17.8 Parts of 3-benzoyl-propionic acid and 8.6 parts of ethylenediamine are heated for 2½ hours at 150°–160°. The crude reaction mass is then dissolved in 25 parts of ethyl acetate, the reaction product is allowed to crystallise out, it is filtered off and recrystallised from a mixture of ethyl acetate and ligroin. The pure 7a-phenyl-hexahydro-5H-pyrrolo[1,2-a]imidazol-5-one of the formula

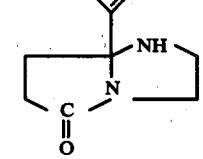

melts at 129.5°.

EXAMPLE 15

17.8 Parts of 3-benzoyl-propionic acid are suspended in 125 parts of chlorobenzene whereupon 8 parts of N-methylethylenediamine are added and the whole is heated for half an hour while distilling off water and chlorobenzene. THe chlorobenzene is then removed in vacuo and the residue is recrystallised, first from ethyl acetate and then from a mixture of ligroin and ethyl acetate. The pure 1-methyl-7a-phenyl-hexahydro-5H-pyrrolo[1,2-a]imidazol-5-one of the formula

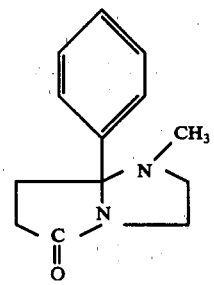

melts at 94°. The following compounds, for example, are produced in an analogous manner:

a) 1-methyl-7a-(p-chlorophenyl)-hexahydro-5H-pyrrolo[1,2-a]imidazol-5-one, M.P. 84°, and
b) 1-methyl-7a-(m-nitrophenyl)-hexahydro-1H-pyrrolo[1,2-a]imidazol-5-one, M.P. 129.5°.

EXAMPLE 16

23.4 Parts of 3-(p.-tert.butyl-benzoyl)-propionic acid and 10 parts of ethylenediamine are heated for 2 hours at 150°–160°. After cooling, the reaction product crystallises from ethyl acetate. The pure 7a-(p-tert.butylphenyl)-hexahydro-5H-pyrrolo[1,2-a]imidazol-5-one of the formula

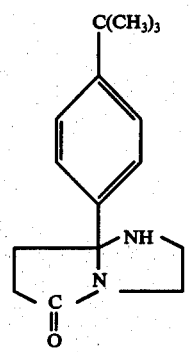

melts at 202°.

The following compounds are produced in an analogous way:

a) 7a-(p-chlorophenyl)-hexahydro-5H-pyrrolo[1,2-a]imidazol-5-one, M.P. 156°;
b) 7a-(p-tolyl)-hexahydro-5H-pyrrolo[1,2-a]imidazol-5-one, M.P. 134.5°;
c) 7a-(p-methoxyphenyl)-hexahydro-5H-pyrrolo[1,2-a]imidazole-5-one, M.P. 147.6°;
d) 7a-(α,α,α-trifluoro-m-tolyl)-hexahydro-5H-pyrrolo[1,2-a]imidazol-5-one, M.P. 119.5°;
e) 7a-(o-hydroxyphenyl)-hexahydro-5H-pyrrolo[1,2-a]imidazol-5-one, M.P. 200°, and
f) 7a-(m-nitrophenyl)-hexahydro-5H-pyrrolo[1,2-a]imidazol-5-one, M.P. 164.5°.

EXAMPLE 17

25.4 Parts of 3-benzoyl-2-phenyl-propionic acid and 8 parts of ethylenediamine are heated for 2 hours at 150°–170°. The cooled reaction mixture is then extracted several times with hot ligroin, the solution obtained is concentrated and the product which precipitates is crystallised from ethyl acetate. The pure 6,7a-diphenyl-hexahydro-5H-pyrrolo[1,2-a]imidazol-5-one of the formula

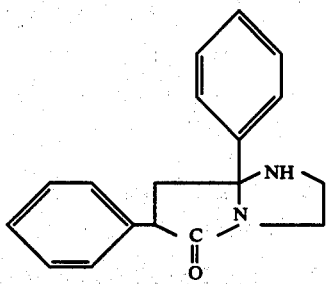

melts at 168°. 6-Phenyl-7a-(4'-methoxyphenyl)-hexahydro-5H-pyrrolo[1,2-a]imidazol-5-one is produced in an analogous manner. It melts at 150°.

EXAMPLE 18

16.4 Parts of o-acetyl-benzoic acid and 7 parts of ethylenediamine are heated in 120 parts of chlorobenzene for 3 hours while distilling off chlorobenzene and the liberated water. Also o-chlorotoluene or similar solvents can be used instead of chlorobenzene. The reaction solution is then concentrated in vacuo, the residue is diluted with ethyl acetate and it is left overnight in the refrigerator to crystallise out. The reaction product is filtered off and purified by recrystallisation from ethyl acetate. The 9b-methyl-1,2,3,9b-tetrahydro-5H-imidazo[2,1-a]isoindol-5-one of the formula

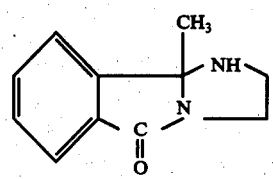

melts at 112°. The following compounds are obtained in an analogous way:

a) 9b-ethyl-1,2,3,9b-tetrahydro-5H-imidazo[2,1-a]isoindol-5-one, M.P. 88°;
b) 9b-benzyl-1,2,3,9b-tetrahydro-5H-imidazo[2,1-a]isoindol-5-one, M.P. 117°;
c) 1,9b-dimethyl-1,2,3,9b-tetrahydro-5H-imidazo[2,1-a]isoindol-5-one, M.P. 74°, and
d) 1-ethyl-9b-methyl-1,2,3,9b-tetrahydro-5H-imidazo[2,1-a]isoindol-5-one, M.P. 79.5°.

EXAMPLE 19

17.8 Parts of o-propionyl-benzoic acid and 11 parts of o-phenylenediamine are heated for 1 hour in 200 parts of chlorobenzene while distilling off water and chlorobenzene. The excess chlorobenzene is then removed in vacuo and the residue is distilled under high vacuum. The destillate solidifies and is recrystallised from a little ethyl acetate. The pure 4b-ethyl-4b,5-dihydro-11H-benzo[4,5]imidazo[2,1-a]isoindol-11-one of the formula

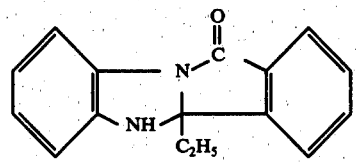

melts at 134°. 4b-methyl-4b,5-dihydro-11H-benzo[4,5]imidazo[2,1-a]isoindol-11-one (M.P. 182.5°) is produced in an analogous manner from o-acetylbenzoic acid and o-phenylenediamine.

EXAMPLE 20

17.8 Parts of 3-benzoyl-propionic acid and 8 parts of 1,3-propanediamine are heated for 2½ hours at 150°–160° and the product obtained is purified by recrystallisation from ethyl acetate. The reaction can also be performed, however, in chlorobenzene while distilling off the mixture of water and chlorobenzene formed. The pure 8a-phenyl-hexahydro-pyrrolo[1,2-a]pyrimidine-6(2H)-one of the formula

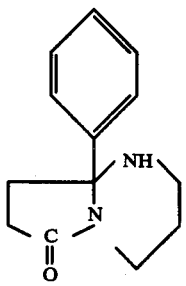

melts at 134°. The following products are obtained in an analogus manner:

a) 8a-(p-chlorophenyl)-hexahydro-pyrrolo[1,2-a]pyrimidin-6(2H)-one, M.P. 125°;
b) 8a-(p-tolyl)-hexahydro-pyrrolo[1,2-a]pyrimidin-6(2H)-one, M.P. 147.5°;
c) 8a-(p-tert.butylphenyl)-hexahydro-pyrrolo[1,2-a]pyrimidin-6(2H)-one, M.P. 178.5°;
d) 8a-(m-chlorophenyl-hexahydro-pyrrolo[1,2-a]pyrimidin-6(2H)-one, M.P. 110°;
e) 8a-(m-tolyl)-hexahydro-pyrrolo[1,2-a]pyrimidin-6(2H)-one, M.P. 92.5°;
f) 7,8a-diphenyl-hexahydro-pyrrolo[1,2-a]pyrimidin-6(2H)-one, M.P. 164.8°;
g) 8a-(o-hydroxyphenyl)-hexahydro-pyrrolo [1,2-a]pyrimidin-6(2H)-one, M.P. 144.5°;
h) 8a-(α,α,α-trifluoro-m-tolyl)-hexahydro-pyrrolo[1,2-a]pyrimidin-6(2H)-one, M.P. 97.5°;
i) 7-phenyl-8a-(p-methoxyphenyl)-hexahydro-pyrrolo[1,2-a]pyrimidin-6(2H)-one, M.P. 156°;
j) 1-methyl-8a-(p-chlorophenyl)-hexahydro-pyrrolo[1,2-a]pyrimidin-6(2H)-one, B.P. 151°-152°/0.05 Torr, and
k) 1-ethyl-8a-(p-chlorophenyl)-hexahydro-pyrrolo[1,2-a]pyrimidin-6(2H)-one, B.P. 151°-153°/0.1 Torr.

EXAMPLE 21

19.2 Parts of 4-benzoyl-butyric acid and 7 parts of ethylenediamine are heated for 2½ hours at 150°. The reaction product is extracted several times with hot ethyl acetate and allowed to crystallise out. On recrystallising from ligroin or ethyl acetate, 8a-phenyl-hexahydro-imidazo[1,2-a]pyridin-5(1H)-one of the formula

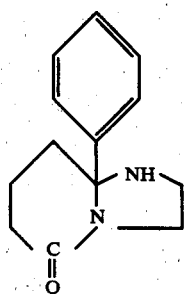

is obtained. It melts at 137°. The following compounds are produced in an analogous manner:

a) 7,7-dimethyl-8a-phenyl-hexahydro-imidazo[1,2-a]pyridin-5(1H)-one, M.P. 99.5°;
b) 6,7-diphenyl-8a-(p-methoxyphenyl)-hexahydro-imidazo[1,2-a]pyridin-5(1H)-one, M.P. 187.5°, and c) 1-methyl-8a-phenyl-hexahydro-imidazo[1,2-a]pyridin-5(1H)-one, B.P. 135°-137°/0.03 Torr.

EXAMPLE 22

20.8 Parts of 3-(p-anisoyl)-propionic acid and 10 parts of 1,4-butanediamine in 180 parts of chlorobenzene are heated in such a way for 2 hours that about half of the chlorobenzene is distilled off. The remainder of the chlorobenzene is then removed in vacuo and the residue is extracted several times with hot ligroin (B.P. 60°-90°) and this solution is concentrated. The crystals so obtained are recrystallised from ligroin. The pure 9a-(p-methoxyphenyl)-octahydro-7H-pyrrolo[2,1-a][1,3]diazepin-7-one of the formula

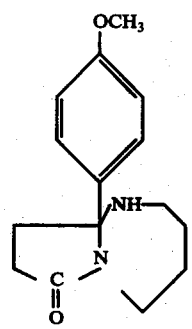

melts at 100.2°. The following compounds are obtained in an analogous manner:

a) 9a-phenyl-octahydro-7H-pyrrolo[2,1-a][1,3]diazepin-7-one, M.P. 109°, and
b) 9a-p-tolyl-octahydro-7H-pyrrolo[1,2-a][1,3]diazepin-7-one, M.P. 104.5°.

EXAMPLE 23

19.2 Parts of 4-benzoyl-butyric acid and 9 parts of 1,3-propanediamine are heated for 2½ hours at 150°-160°. The reaction mixture is cooled to about 60°, extracted with hot ethyl acetate and the solution obtained is clarified over charcoal. On concentrating, the reaction product precipitates and is purified by recrystallisation from ethyl acetate. The melting point of the 9a-phenyl-octahydro-6H-pyrido[1,2-a]pyrimidin -6-one of the formula

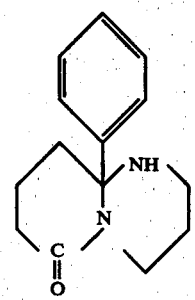

obtained is 142.5°. The following compound is obtained in an analogous manner:

8,8-dimethyl-9a-phenyl-octahydro-6H-pyrido[1,2-a]pyrimidin -6-one, M.P. 120°.

EXAMPLE 24

16.4 Parts of o-acetyl-benzoic acid and 8 parts of 1,3-propanediamine are heated for 2 hours at 150°–160°. The reaction mixture is then distilled under high vacuum. The 10b-methyl-1,3,4,10b-tetrahydro-pyrimido[2,1-a]isoindol -6(2H)-one obtained of the formula

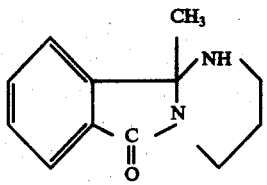

boils at 120°–123°/0.1 Torr. After recrystallising from ethyl acetate/benzine, it melts at 64.5°. The following compounds are obtained in an analogous manner:

a) 10b-ethyl-1,3,4,10b-tetrahydro-pyrimido[2,1a]isoindol -6(2H)-one, M.P. 127.5°;
b) 10b-benzyl-1,3,4,10b-tetrahydro-pyrimido[2,1-a]isoindol -6(2H)-one, M.P. 131°, and
c) 1,10b-dimethyl-1,3,4,10-b-tetrahydro-pyrimido[2,1-a]isoindol-6(2H)-one, B.P. 121°–123°/0.05 Torr.

EXAMPLE 25

16.4 Parts of o-acetyl-benzoic acid and 13.2 parts of 1,4-butanediamine are heated for 3 hours at 160°–180°. After cooling, the reaction mass is extracted with ethyl acetate and brought to crystallisation by concentrating the solvent. The melting point of the recrystallised 11b-methyl-1,2,3,4,5,11b-hexahydro 7H-[1,3]diazepino[2,1-a]isoindol -7-one of the formula

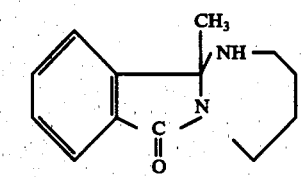

is 136.5°.

EXAMPLE 26

23.2 Parts of 2-benzoyl-cyclohexane carboxylic acid, 100 parts by volume of o-chlorotoluene and 7.2 parts of ethylenediamine are heated for 2 hours at 160°, whereby the reaction water and a part of the o-chlorotoluene is distilled off. The reaction mass is then evaporated to dryness in vacuo and the residue is recrystallised from a mixture of chlorohexane and ethyl acetate. In this way, 9b-phenyl-decahydro-5H-imidazo[2,1a]isoindol -5-one of the formula

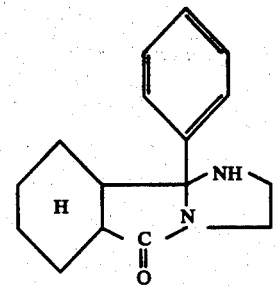

is obtained. It melts at 136°–137°. On using 1,3-propanediamine instead of the ethylenediamine, 10b-phenyl-decahydro-pyrimido [2,1-a]isoindol -6(6aH)-one of the formula

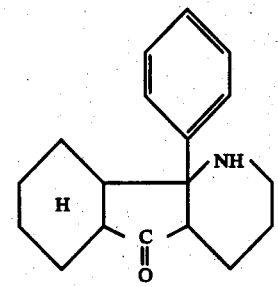

is obtained in an analogous manner. M.P. 169°–172°.

We claim:
1. A compound of the formula

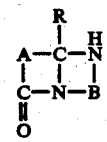

wherein R is aryl of the formula

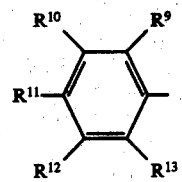

each of $R^9$, $R^{10}$, $R^{11}$, $R^{12}$ and $R^{13}$ is a member selected from the group consisting of a hydrogen atom, a chlorine atom, a fluorine atom, a bromine atom, lower alkyl, lower alkoxy, trifluoromethyl and lower alkylthio; A is trimethylene and B is trimethylene.

2. A compound of the formula:

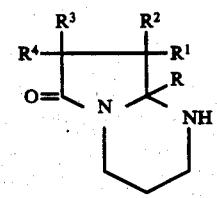

wherein R is aryl of the formula:

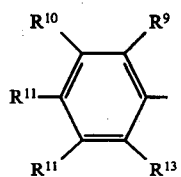

each of $R^1$, $R^2$, $R^3$ and $R^4$ is a member selected from the group consisting of a hydrogen atom, lower straight chain alkyl, or phenyl; and each of $R^9$, $R^{10}$, $R^{11}$, $R^{12}$ and $R^{13}$ is a member selected from the group consisting of a hydrogen atom, a chlorine atom, a fluorine atom, a bromine atom, lower alkyl, lower alkoxy, trifluoromethyl and lower alkylthio.

3. 8a-phenyl-1,2,3,4,6,7,8,8a-octahydro-pyrrolo[1,2-a]pyrimidin-6-one.

4. 8a-(p-chlorophenyl)-hexahydro-pyrrolo[1,2-a]pyrimidin-6(2H)-one.

5. 9a-phenyl-octahydro-6H-pyrido[1,2-a]pyrimidin-6-one.

* * * * *